(12) United States Patent
Sun et al.

(10) Patent No.: US 11,152,098 B2
(45) Date of Patent: *Oct. 19, 2021

(54) SYSTEM AND METHOD FOR HEALTH DATA MANAGEMENT WITH WEARABLE DEVICES

(71) Applicant: International Business Machines Corporation, Armonk, NY (US)

(72) Inventors: Lin Sun, Cary, NC (US); Liam S. Harpur, Dublin (IE); Paul R. Bastide, Boxford, MA (US); Matthew E. Broomhall, Goffstown, NH (US)

(73) Assignee: International Business Machines Corporation, Armonk, NY (US)

( * ) Notice: Subject to any disclaimer, the term of this patent is extended or adjusted under 35 U.S.C. 154(b) by 483 days.

This patent is subject to a terminal disclaimer.

(21) Appl. No.: 15/919,356

(22) Filed: Mar. 13, 2018

(65) Prior Publication Data

US 2019/0287669 A1   Sep. 19, 2019

(51) Int. Cl.
*G16H 20/30* (2018.01)
*G16H 10/60* (2018.01)
(Continued)

(52) U.S. Cl.
CPC .......... *G16H 20/30* (2018.01); *A61B 5/6801* (2013.01); *A63B 24/0062* (2013.01);
(Continued)

(58) Field of Classification Search
CPC ........ G16H 50/30; G16H 20/00; G16H 20/30; G06F 19/30; G06F 21/84; A61B 5/6801
See application file for complete search history.

(56) References Cited

U.S. PATENT DOCUMENTS 9,730,027 B2   8/2017   Su et al.
2014/0163927 A1 *   6/2014   Molettiere ........... A61B 5/0002
702/189
(Continued)

FOREIGN PATENT DOCUMENTS

EP           3073399 A1 *   9/2016   ............. G16H 20/60
EP           3073399 A1       9/2016
WO    2016/157217 A2    10/2016

OTHER PUBLICATIONS

Gruenwald et al., "Using Data Mining to Estimate Missing Sensor Data", IEEE DOI 10.1109/ICDMW.2007.103, pp. 207-212 (Year: 2007) (Year: 2007).*

(Continued)

*Primary Examiner* — Elaine Gort
*Assistant Examiner* — Constantine B Siozopoulos
(74) *Attorney, Agent, or Firm* — Scott S. Dobson; Maxine L. Barasch; Keohane & D'Alessandro, PLLC

(57) ABSTRACT

Disclosed embodiments provide techniques for identifying gaps in health management data, and combining an estimated data subset with the health management data to fill in gaps in the health management data. The health management data can be derived from a wearable electronic fitness tracking device such as a smart watch or pedometer. The estimated data subset can be derived based on historical data for the individual, average data for a demographic group, crowdsourced, or estimated based on user profile information, and/or portable electronic device information, such as from a smartphone belonging to a user. The estimated data subset is combined with the health management data to form a revised health parameter dataset. The estimated data subset may be sent to a wearable electronic fitness tracking device, which causes the wearable electronic fitness tracking device (Continued)

to initiate a fitness program adjustment based on the revised health parameter dataset.

14 Claims, 9 Drawing Sheets

(51) Int. Cl.
    *A63B 24/00*         (2006.01)
    *A61B 5/00*         (2006.01)

(52) U.S. Cl.
    CPC ......... *A63B 24/0075* (2013.01); *G16H 10/60* (2018.01); *A63B 2024/0065* (2013.01)

(56) References Cited

U.S. PATENT DOCUMENTS

| | | |
|---|---|---|
| 2015/0220883 A1 | 8/2015 | B'Far et al. |
| 2015/0289820 A1* | 10/2015 | Miller ............... A61B 5/1495 600/300 |
| 2015/0324751 A1* | 11/2015 | Orenstein ......... G06F 19/3481 702/3 |
| 2016/0019283 A1 | 1/2016 | Gibson et al. |
| 2016/0114214 A1* | 4/2016 | Ellis ..................... G06F 11/328 434/255 |
| 2016/0173359 A1 | 6/2016 | Brenner et al. |
| 2017/0039480 A1 | 2/2017 | Bitran et al. |
| 2018/0068033 A1* | 3/2018 | Bandyopadhyay ......................... G06F 16/90348 |
| 2018/0314573 A1* | 11/2018 | Chang ............... G06F 11/3452 |

OTHER PUBLICATIONS

Gruenwald et al "Using Data Mining to Estimate Missing Sensor Data", IEEE DOI 10.1109/ICDMW.2007.103, pp. 207-212 (Year: 2007).*

Denecke, Kerstin. "Integrating social media and mobile sensor data for clinical decision support: Concept and requirements." (2016): 562-566. (Year: 2016).*

Appendix P, "List of IBM Patents or Patent Applications Treated as Related", Mar. 25, 2020, 2 pages.

Shujaat Hussain et al., "A wearable device-based personalized big data analysis model", http://uclab.khu.ac.kr/resources/publication/C_304.pdf, 8 pages.

Ghahremani et al., The Prediction of Physical Activity Intention and Behavior in Elderly Male Residents of a Nursing Home: A Comparison of Two Behavioral Theories, Iran J. Med. Sci., Mar. 2012, https://www.ncbi.nlm.nih.gov/pmc/articles/PMC3470291/, 11 pages.

Mysight360, "Wearable VR Camera for Smooth Panoramic Videos", https://www.kickstarter.com/projects/660471689/mysight360-worlds-first-wearable-vr-camera-for-hik/comments?, Kickstarter, PBC, Copyright 2018, 17 pages.

Armand Tecco, "Why is Exercise Important?", Copyright 2017 Health Discovery Network, http://www.healthdiscovery.net/articles/exercise_importa.htm, 9 pages.

Paul Lamkin, Forbes / Tech, "Wearable Tech Market To Be Worth $34 Billion By 2020", Feb. 17, 2016, 2 pages.

Smoothwearable, http://www.smooth-wearable.com/en/, Copyright 2018 Smooth Wearable, 6 pages.

Gruenwald et al., "Using Data Mining to Estimate Missing Sensor Data", IEEE DOI 10.1109/ICDMW.2007.13, pp. 207-212 (Year: 2007).

Siozopoulos, Constantine B., U.S. Appl. No. 16/520,724, Office Action dated Oct. 5, 2020, 36 pgs.

Constantine B. Siozopoulos, USPTO Final Office Action, dated Mar. 12, 2021, U.S. Appl. No. 16/520,724, 30 pages.

Denecke, Kerstin, "Integrating Social Media and Mobile Sensor Data for Clinical Decision Support: Concept and Requirements", Nursing Informatics, 2016, pp. 562-566.

Siozopoulos, Constantine B., U.S. Appl. No. 16/520,724, Notice of Allowance dated Jun. 24, 2021, 14 pgs.

\* cited by examiner

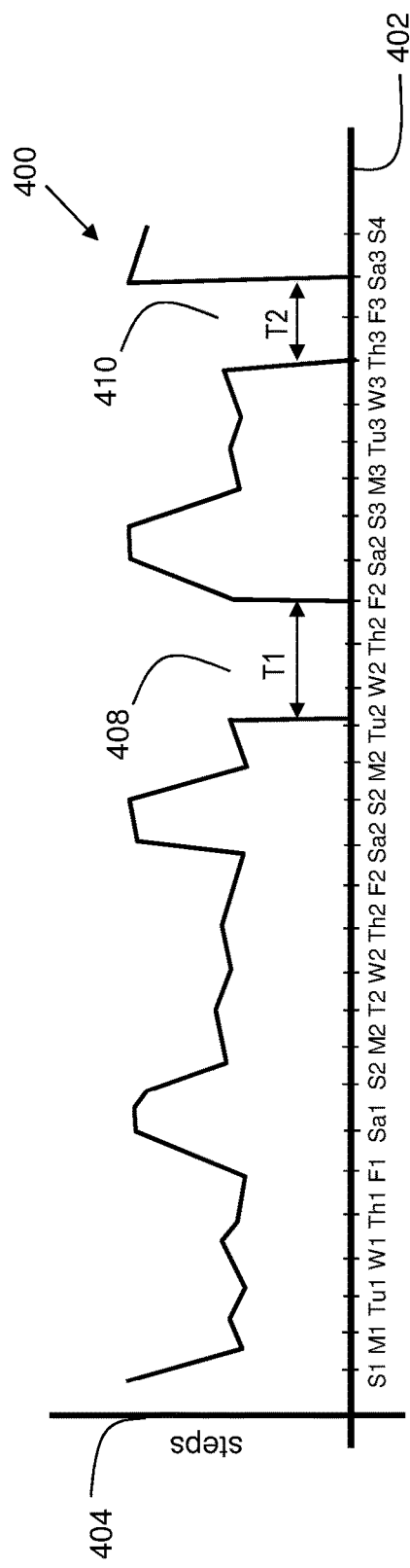
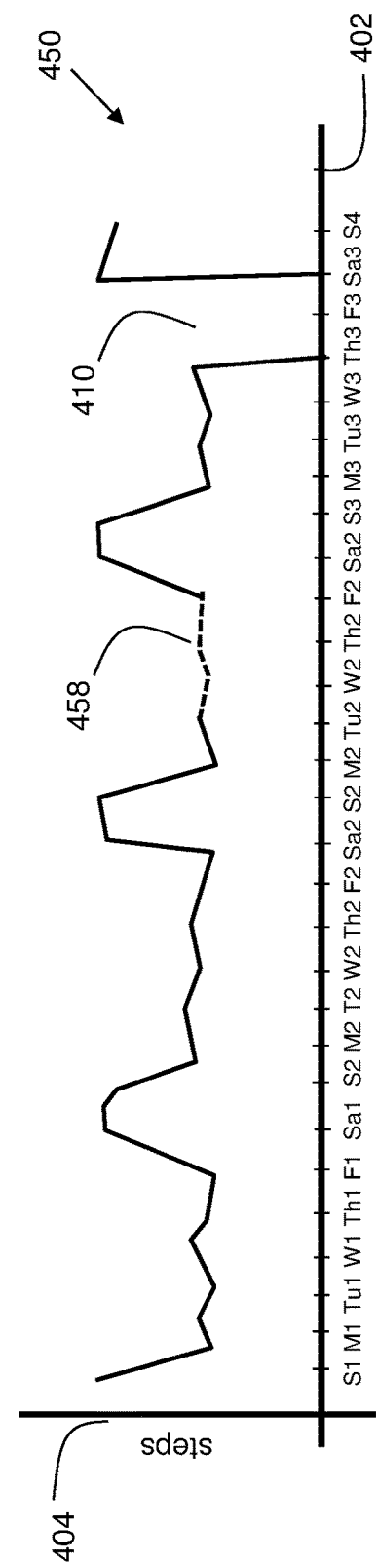
FIG. 4A
FIG. 4B

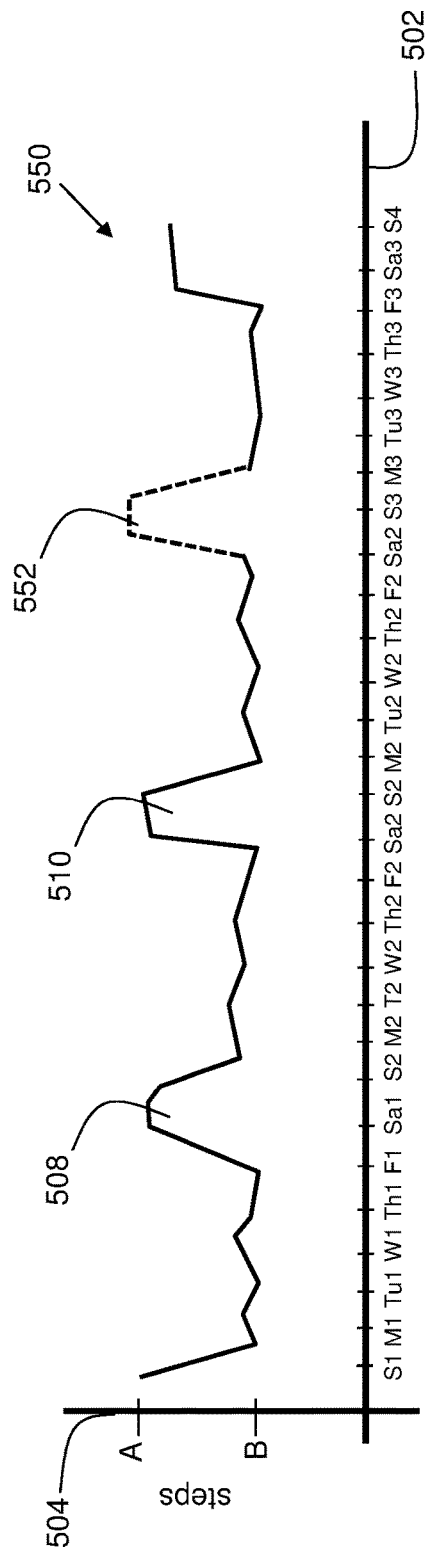
FIG. 5A
FIG. 5B

SYSTEM AND METHOD FOR HEALTH DATA MANAGEMENT WITH WEARABLE DEVICES

FIELD OF THE INVENTION

This invention relates generally to health data management, and more particularly, to systems and methods for health data management with wearable devices.

BACKGROUND

Many people use wearable devices, such as fitness trackers, to track biometric data. Typically, the device is worn as a bracelet or necklace, such that a sensor is touching the user's body. The sensor is included in the device to measure steps the user takes, heart rate of the user, pulse of the user, and other similar data. Fitness trackers are used to monitor progress in, for example, an exercise routine, a distance traveled each day, or other metrics. The data from such fitness trackers is becoming increasingly important for health and wellness assessments. Accordingly, there exists a need for improvements in fitness tracking devices and systems.

SUMMARY

In one embodiment, there is provided a computer implemented method for health data management, comprising: detecting a data gap from a health parameter dataset associated with a user; determining a time duration corresponding to the data gap; computing an estimated data subset for the data gap; and combining the estimated data subset with the health parameter dataset to create a revised health parameter dataset.

In another embodiment, there is provided an electronic computation device comprising: a processor; a memory coupled to the processor, the memory containing instructions, that when executed by the processor, perform the steps of: detecting a data gap from a health parameter dataset associated with a user; determining a missing data time duration corresponding to the data gap; computing an estimated data subset for the data gap; and combining the estimated data subset with the health parameter dataset to create a revised health parameter dataset.

In yet another embodiment, there is provided a computer program product for an electronic computation device comprising a computer readable storage medium having program instructions embodied therewith, the program instructions executable by a processor to cause the electronic computation device to: detect a data gap from a health parameter dataset associated with a user; determine a missing data time duration corresponding to the data gap; compute an estimated data subset for the data gap; and combine the estimated data subset with the health parameter dataset to create a revised health parameter dataset.

BRIEF DESCRIPTION OF THE DRAWINGS

Features of the disclosed embodiments will be more readily understood from the following detailed description of the various aspects of the invention taken in conjunction with the accompanying drawings.

FIG. 4A shows an example of a data gap from a health parameter dataset.

FIG. 4B shows an example of a revised health parameter dataset based on the health parameter dataset of FIG. 4A.

FIG. 5A shows another example of a data gap from a health parameter dataset.

FIG. 5B shows an example of a revised health parameter dataset based on the health parameter dataset of FIG. 5A.

Figure 1:
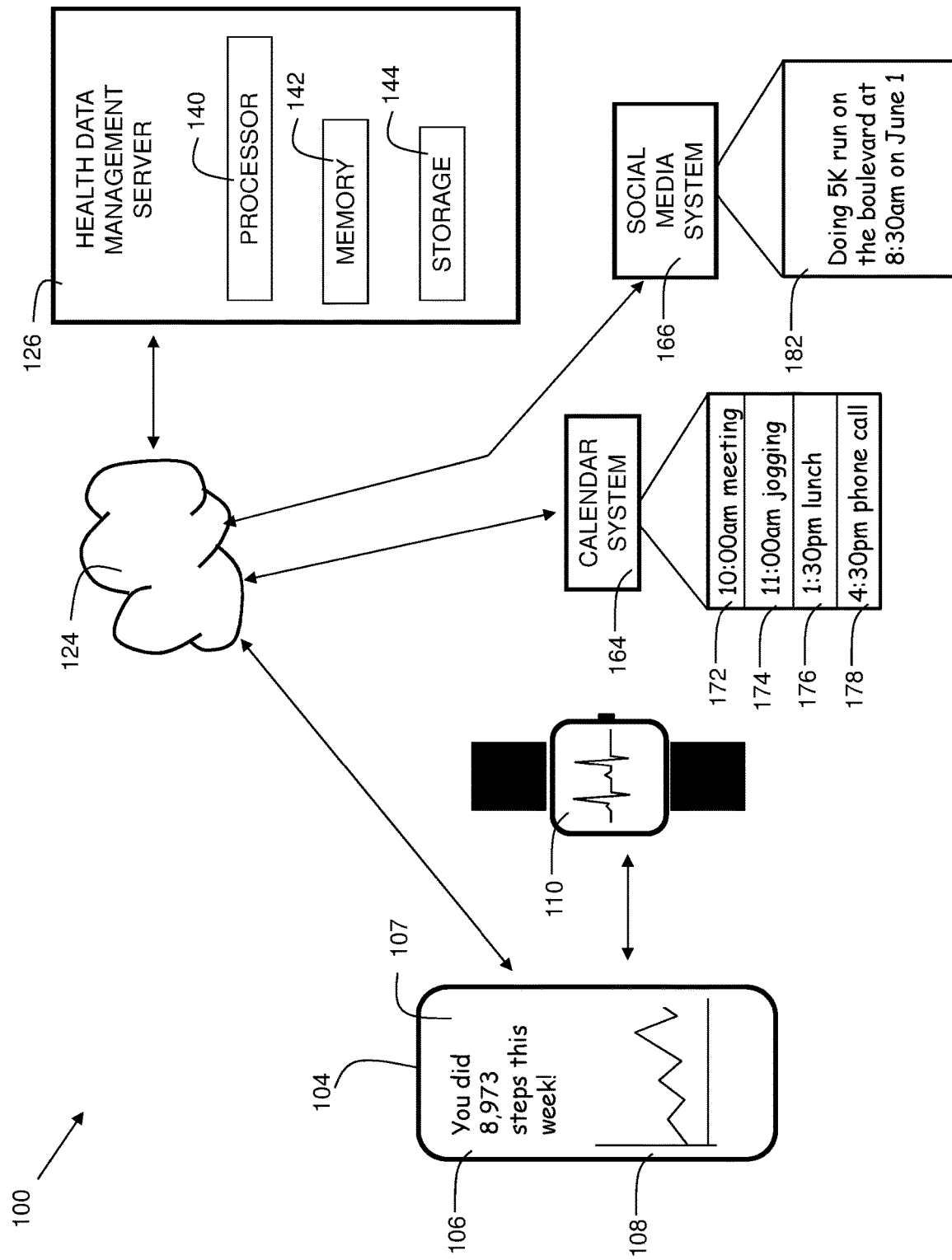
FIG. 1 is a diagram of an environment for embodiments of the present invention.

The drawings are not necessarily to scale. The drawings are merely representations, not necessarily intended to portray specific parameters of the invention. The drawings are intended to depict only example embodiments of the invention, and therefore should not be considered as limiting in scope. In the drawings, like numbering may represent like elements. Furthermore, certain elements in some of the figures may be omitted, or illustrated not-to-scale, for illustrative clarity.

DETAILED DESCRIPTION

Fitness trackers are used to monitor progress in physical activity. It can be difficult to accurately monitor such progress when sometimes a user will forget to wear the fitness tracker, or the fitness tracker may malfunction, etc. This leaves missing data. Accordingly, there exists a need for improvements in fitness tracking devices and systems.

Disclosed embodiments provide techniques for identifying gaps in health management data, and combining an estimated data subset with the health management data to fill in gaps in the health management data. The health management data can be derived from a wearable electronic fitness tracking device such as a smart watch or pedometer. The estimated data subset can be derived based on historical data for the individual, average data for a demographic group, crowdsourced, or estimated based on user profile information, and/or portable electronic device information, such as from a smartphone belonging to a user. The estimated data subset is combined with the health management data to form a revised health parameter dataset. The estimated data subset may be sent to a wearable electronic fitness tracking device, which causes the wearable electronic fitness tracking device to initiate a fitness program adjustment based on the revised health parameter dataset.

Reference throughout this specification to "one embodiment," "an embodiment," "some embodiments", or similar language means that a particular feature, structure, or characteristic described in connection with the embodiment is included in at least one embodiment of the present invention. Thus, appearances of the phrases "in one embodiment," "in an embodiment," "in some embodiments", and similar language throughout this specification may, but do not necessarily, all refer to the same embodiment.

Moreover, the described features, structures, or characteristics of the invention may be combined in any suitable manner in one or more embodiments. It will be apparent to those skilled in the art that various modifications and variations can be made to the present invention without departing from the spirit and scope and purpose of the invention. Thus, it is intended that the present invention cover the modifications and variations of this invention provided they come within the scope of the appended claims and their equivalents. Reference will now be made in detail to the preferred embodiments of the invention.

The terminology used herein is for the purpose of describing particular embodiments only and is not intended to be limiting of this disclosure. As used herein, the singular forms "a", "an", and "the" are intended to include the plural forms as well, unless the context clearly indicates otherwise. Furthermore, the use of the terms "a", "an", etc., do not denote a limitation of quantity, but rather denote the presence of at least one of the referenced items. The term "set" is intended to mean a quantity of at least one. It will be further understood that the terms "comprises" and/or "comprising", or "includes" and/or "including", or "has" and/or "having", when used in this specification, specify the presence of stated features, regions, integers, steps, operations, elements, and/or components, but do not preclude the presence or addition of one or more other features, regions, or elements.

FIG. 1 is a diagram 100 of an environment for embodiments of the present invention. Health data management server 126 has a processor 140, memory 142, and storage 144. Memory 142 includes instructions thereon, which when executed by the processor perform steps of the present invention. Server 126 is an electronic computation device. Server 126 is in communication with network 124. Network 124 may be the Internet, a wide area network, a local area network, or other suitable network.

Mobile device 104 is in communication with server 126 through the network 124. Mobile device 104 may be a smartphone, tablet computer, laptop computer, or other suitable device. Wearable device 110 is in communication with mobile device 104 via near field communication, such as Bluetooth® or other suitable interface. The wearable device 110 may be attached to a user's body at the wrist with a band like a watch. Alternatively, the wearable device 110 may be attached to a user's body around the neck with a tether like a necklace. Yet further, the wearable device 110 may be attached to a user's body around a finger like a ring. Any suitable wearable device attachment mechanism is included within the scope of the invention. Mobile device 104 has a screen 107 on which data may be shown. In the example, on screen 107, there is shown comment 106, which says, "You did 8,973 steps this week!" and a graph 108 of the data.

In some embodiments, calendar system 164 is also in communication with server 126 through the network 124. Calendar system 164 may include a calendaring software program. The program may maintain a user's schedule, such as dates and times of workouts, meetings, or other items. In the example, the user has on its schedule a meeting at entry 172 at 10 am, a jog at entry 174 at 11 am, a lunch at entry 176 at 1:30 pm, and a phone call at entry 178 at 4:30 pm.

In some embodiments, social media system 166 is also in communication with server 126 through the network 124. Social media system 166 may allow various users to create accounts to which they can post personal information. The user's account includes a profile where the information is displayed and can, in some cases, be viewed by other users. Examples of social media systems include but are not limited to Facebook®, Twitter®, LinkedIn®, or other suitable system. A user may post text, images, videos, or other items of content to his/her account for other users to see. In the example, the user has made one post 182 to his/her account, which recites, "Doing 5K run on the boulevard at 8:30 am on June 1."

Embodiments may utilize computerized natural language processing to read calendar entries that pertain to fitness events from calendar system 164 or social media system 166 that is associated with a user to identify possible data gaps. An entry can include one or more keywords. In embodiments, a machine learning natural language analysis of the text in the entry is performed. The natural language analysis may include, but is not limited to, indexing, concordance, stop word processing, bigram processing, dispersion analysis, lexical richness analysis (ratio of distinct words to total words), disambiguation, part-of-speech analysis, anaphora resolution (the process of identifying what a pronoun or noun phrase refers to), or any other suitable process.

In the example shown in FIG. 1, in entry 174 on the calendar, embodiments can detect the word "jogging." In post 182 on the social media system, embodiments can detect the word "run." The server can, using natural language processing, detect keywords associating an event indicating some activity that day (since jogging or a run would mean that many steps should be detected). Accordingly, if there is a data gap that day, embodiments supplement the health parameter dataset with estimated data. In some embodiments, the supplementation is in response to detection of the data gap and detection of a simultaneous entry indicating an event. In other embodiments, a confirmation request is sent to the user, and supplementation occurs only if the user responds with a positive affirmation.

Figure 2:
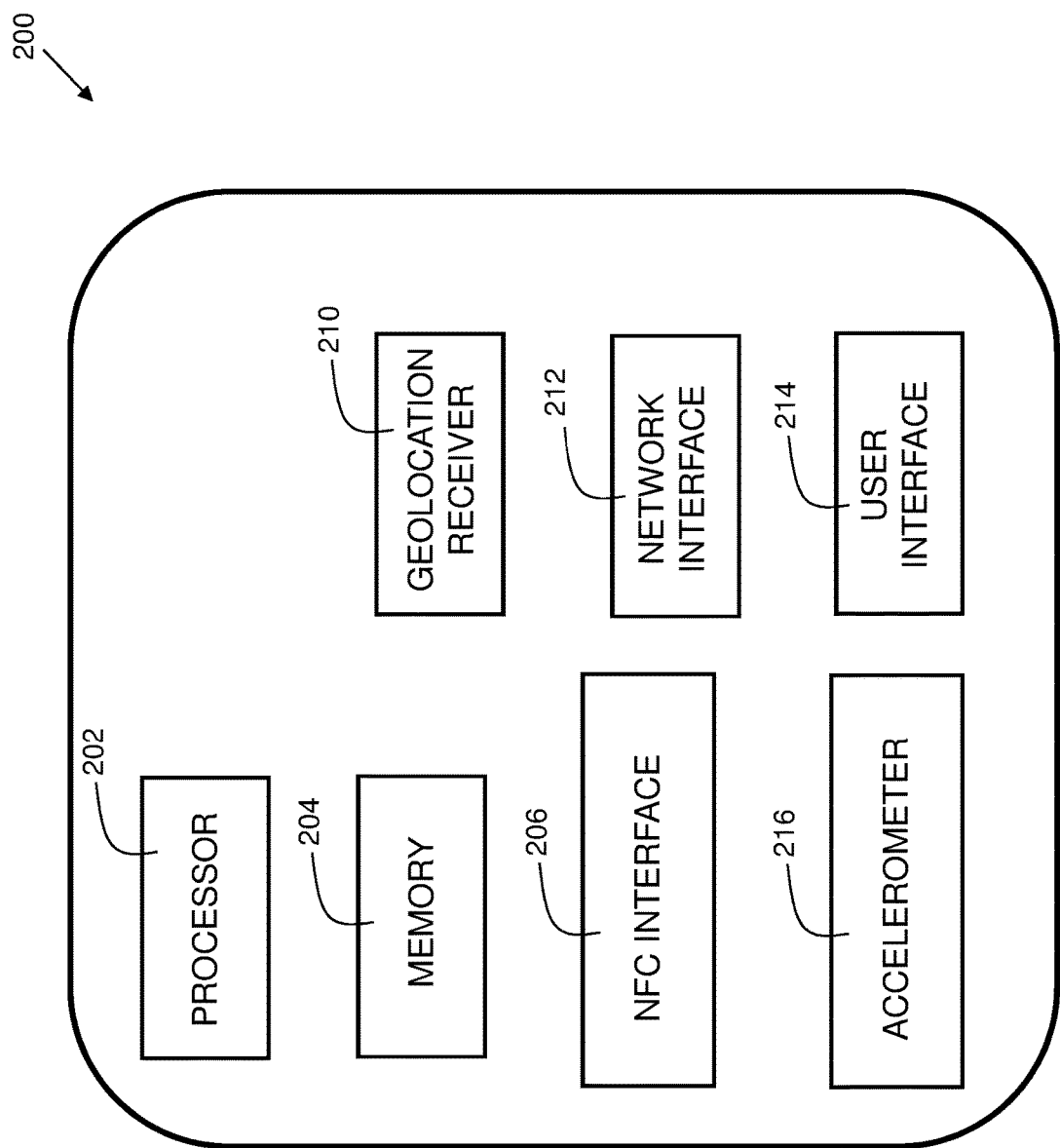
FIG. 2 is a block diagram of a client device in accordance with embodiments of the present invention.

FIG. 2 is a block diagram of a client device in accordance with embodiments of the present invention. Device 200 is a mobile device. Device 200 includes a processor 202, which is coupled to a memory 204. Memory 204 may include dynamic random access memory (DRAM), static random access memory (SRAM), magnetic storage, and/or a read only memory such as flash, EEPROM, optical storage, or other suitable memory. In some embodiments, the memory 204 may not be a transitory signal per se. Memory 204 stores instructions, which when executed by the processor, implement steps of embodiments of the present invention.

Device 200 further includes a near field communication interface 206. In embodiments, this may be a Bluetooth® transceiver, Zigbee® transceiver, or other suitable interface.

Device 200 further includes an accelerometer 216. The accelerometer may be a capacitive, piezoelectric resistive, or other suitable type.

Device 200 further includes geolocation receiver 210. The geolocation receiver can be for a global positioning system (GPS), GLONASS, Galileo, or other suitable system that provides autonomous geo-spatial positioning.

The device 200 further includes a network interface 212. The network interface 212 may be a wireless communication interface that includes modulators, demodulators, and/or antennas for a variety of wireless protocols including, but not limited to, Wi-Fi and/or cellular communication protocols for communication over a computer network.

Device 200 further includes a user interface 214, examples of which include a liquid crystal display (LCD), a plasma display, a cathode ray tube (CRT) display, a light emitting diode (LED) display, an organic LED (OLED)

display, or other suitable display technology. The user interface 214 may further include a keyboard, mouse, or other suitable human interface device. In some embodiments, user interface 214 may be a touch screen, incorporating a capacitive or resistive touch screen in some embodiments.

Figure 3:
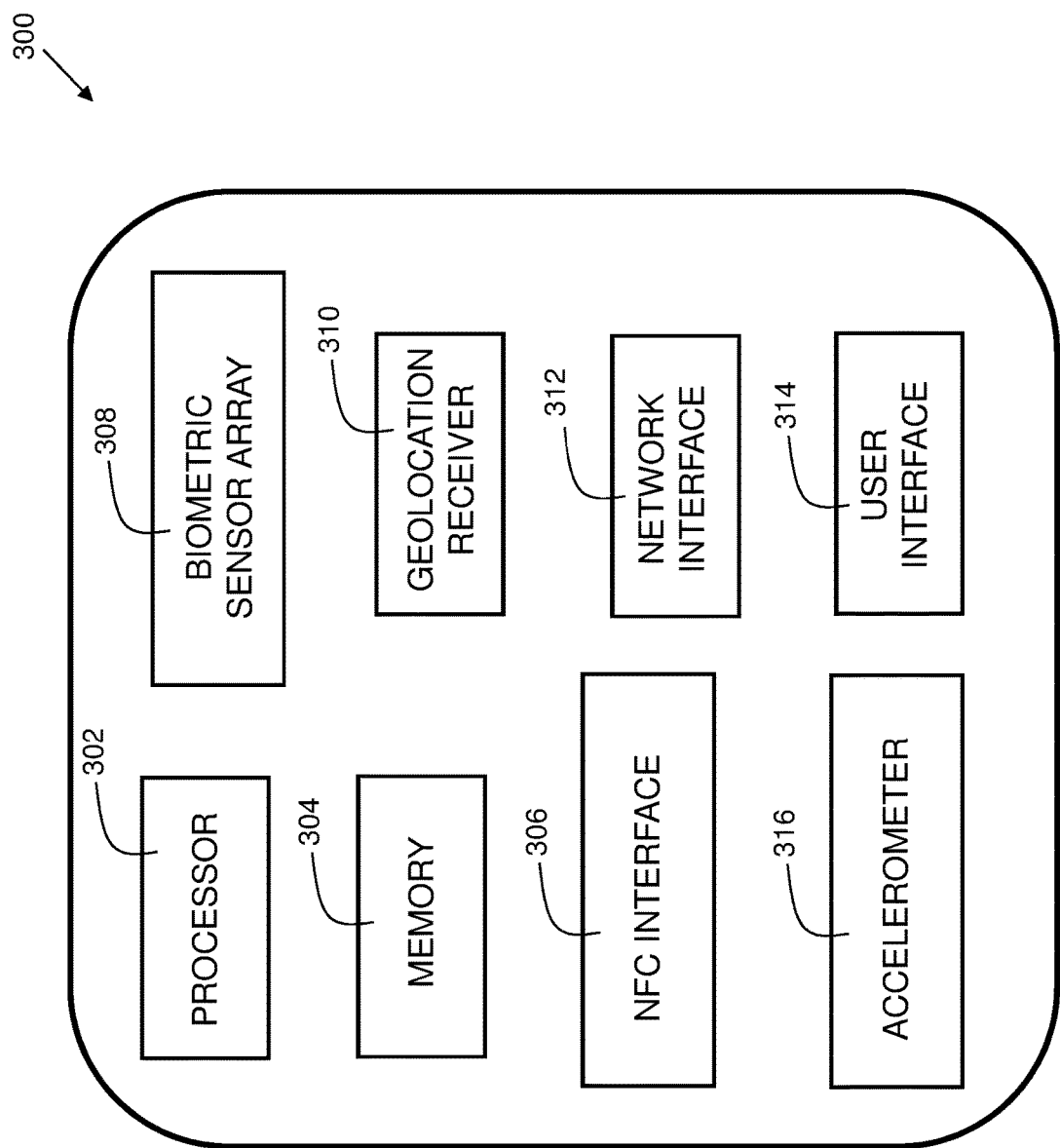
FIG. 3 is a block diagram of a wearable electronic fitness tracking device in accordance with embodiments of the present invention.

FIG. 3 is a block diagram of a wearable electronic fitness tracking device 300 in accordance with embodiments of the present invention. Device 300 includes a processor 302, which is coupled to a memory 304. Memory 304 may include dynamic random access memory (DRAM), static random access memory (SRAM), magnetic storage, and/or a read only memory such as flash, EEPROM, optical storage, or other suitable memory. In some embodiments, the memory 304 may not be a transitory signal per se. Memory 304 stores instructions, which when executed by the processor, implement steps of embodiments of the present invention.

Device 300 further includes a near field communication interface 306. In embodiments, this may be a Bluetooth® transceiver, Zigbee® transceiver, or another suitable interface.

Device 300 further includes a biometric sensor array 308. In some embodiments, this can be an infrared sensor, an electronic sensor, an accelerometer, or another suitable type of sensor. In some embodiments, the sensor array may include a pulse sensor, oxygenation sensor, heartrate sensor, temperature sensor, a pedometer, or other suitable sensor. A pulse sensor may use an infrared light. The sensor may detect the user's pulse by the amount of IR light reflected from the bloodstream. A pedometer may use an accelerometer to detect the swings of a user's body as s/he walks. Each swing is registered as a step.

Device 300 further includes an accelerometer 316. The accelerometer may be a capacitive, piezoelectric resistive, or other suitable type.

Device 300 further includes geolocation receiver 310. The geolocation receiver can be for a global positioning system (GPS), GLONASS, Galileo, or other suitable system that provides autonomous geo-spatial positioning.

The device 300 further includes a network interface 312. The network interface 312 may be a wireless communication interface that includes modulators, demodulators, and/or antennas for a variety of wireless protocols including, but not limited to, Wi-Fi and/or cellular communication protocols for communication over a computer network.

Device 300 further includes a user interface 314, examples of which include a liquid crystal display (LCD), a plasma display, a light emitting diode (LED) display, an organic LED (OLED) display, or other suitable display technology. The user interface 314 may further include a touch screen (incorporating a capacitive or resistive touch screen in some embodiments), and/or one or more buttons, or other suitable human interface device.

FIG. 4A shows an example of a health parameter dataset. The health parameter dataset is shown on graph 400 with dates on x-axis 402 and steps detected from a user on y-axis 404. The x-axis indicates days of the week for three weeks with an "S," plus a number, denotes a Sunday and an "Sa," plus a number, denotes a Saturday, with the other days therein between. The number indicates first week, second week, third week, etc. In the example, the health parameter dataset includes a user's steps detected from a pedometer of a wearable device 110 (FIG. 1) worn by the user, and sent to server 126 (FIG. 1). Accordingly, the graph shows the number of steps detected from the user per day. In embodiments, a data gap (i.e., missing subset of data) is detected in the health parameter dataset.

In some embodiments, detecting a data gap includes identifying an instance of a data gap of a time duration that exceeds a predetermined threshold. For example, a break of eight hours in a 24-hour period may not be considered enough to constitute a data gap for pedometer data since it would be viewed as normal for the user to remove the wearable device before sleeping. In contrast, a break of more than one hour for a pulse detector may constitute a data gap as it means the device was probably removed or broken.

In the example, the duration to trigger a gap is 24 hours. Two data gaps are present in the detected data—A first gap 408 of time duration T1, and a second gap 410 of time duration T2. T1 denotes a gap for two days—W2 and Th2. T2 denotes a gap for one day (a Friday), F3. The data may not have been captured for any of a number of reasons. For example, the user may have forgotten to wear the wearable device on one or more of those days. Alternatively, the wearable device may be broken, or the NFC device within the wearable device is malfunctioning. If the wearable device, or a portion thereof, is not working properly, the detection or communication of data to the mobile device (and server) may be interrupted.

FIG. 4B shows an example of a revised health parameter dataset based on the health parameter dataset of FIG. 4A. In embodiments, gaps in data may be supplemented with estimated data. In some embodiments, historical health data may be retrieved for the user, and the historical health data used as the estimated data subset. Graph 450 shows the gap denoted as T1 in FIG. 4A supplemented with data estimate 458. In some embodiments, the supplemental estimate is calculated by averaging the historical data for a predetermined time duration. In the example, historical data of steps for the previous 2.5 weeks (from S1 to Tu2) was accessed and an average thereof calculated.

In some embodiments, where the missing health data is the number of steps taken, for example, location analysis may be used to fill in data gaps. A first location for the user may be determined where the first location corresponds to a start of the data gap. A second location for the user may be determined where the second location corresponds to an end of the data gap. A distance between the first location and second location may be determined; and health data may be estimated for the user based on the distance. The locations for the user may be detected using a geolocation receiver 210 of FIG. 2 of the user's mobile device. As an example, embodiments may detect that a user travelled a mile between the first location and the second location, and compute an estimate of steps taken based on that computed distance as 2,300 steps. This estimate can be based on previous data for that user, average data for a demographic group, or other suitable data. In some embodiments, estimating health data for the user based on the distance is based on profile data for the user, such as the user's height or stride information. Embodiments estimate a number of steps a user would have taken if s/he walked the distance between the two locations.

In some embodiments, gaps in the data may only be supplemented if the gap exceeds a predetermined duration. In the example, the predetermined duration for supplementation is 40 hours. Accordingly, only gap T1 is supplemented since gap T2, at a duration of 24 hours, does not exceed the 40-hour threshold. Thus, in embodiments, detecting a data gap from a health parameter dataset comprises identifying an instance of a data gap time duration that exceeds a predetermined threshold.

FIG. 5A shows another example of a health parameter dataset. Graph 500 shows dates on x-axis 502 and steps detected from a user on y-axis 504. Accordingly, the graph shows the number of steps detected from the user per day. The x-axis indicates days of the week for three weeks with an "S," plus a number, denotes a Sunday and an "Sa," plus a number, denotes a Saturday, with the other days therein between. The number indicates first week, second week, third week, etc. In implementations, the steps are detected from a pedometer of a wearable device worn by the user, and sent to server 126 (FIG. 1). In some embodiments, detecting missing data from a health parameter dataset includes identifying a periodic health parameter pattern, and identifying an instance of a data gap that overlaps a period corresponding to the periodic health parameter pattern. In the example, the periodic health parameter pattern is a spike on Saturdays and Sundays. Mondays through Fridays, the health parameter is around reference point B. The number of steps steeply increases on Saturdays and Sundays through to reference point A. The first increase is shown as 508, and the second increase is shown as 510. A data gap 512 is detected. The data gap 512 occurs on S3 (Sunday).

FIG. 5B shows an example of a revised health parameter dataset based on the health parameter dataset of FIG. 5A. As shown, the section where the data gap 512 was detected is supplemented with reconstructed data 552. The reconstructed data is at reference point A, since based on the pattern, server 126 (FIG. 1) determines that data captured on Saturdays and Sundays is usually at reference point A instead of reference point B or another point.

Figure 6A:
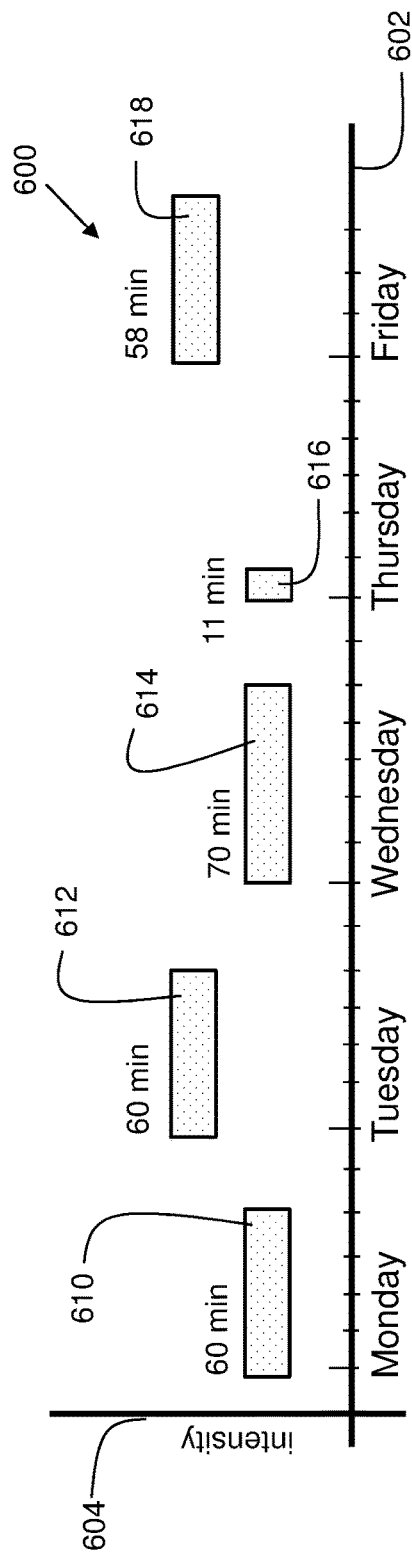
FIG. 6A shows another example of a data gap from a health parameter dataset.

FIG. 6A shows another example of a health parameter dataset. In the example, graph 600 is shown with days on the x-axis 602, and intensity on the y-axis 604. On Monday, at 610, 60 minutes of activity is detected. On Tuesday, at 612, 60 minutes of activity is detected. On Wednesday, at 614, 70 minutes of activity is detected. On Thursday, at 616, 11 minutes of activity is detected. On Friday, at 618, 58 minutes of activity is detected.

Figure 6B:
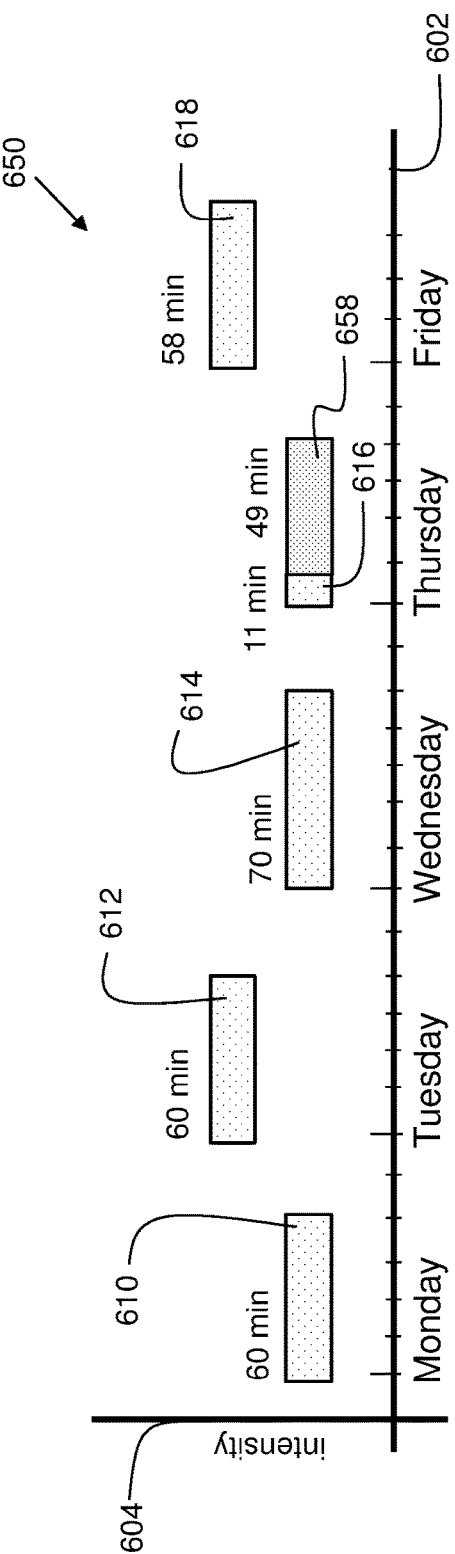
FIG. 6B shows an example of a revised health parameter dataset based on the health parameter dataset of FIG. 6A.

FIG. 6B shows an example of a revised health parameter dataset based on the health parameter dataset of FIG. 6A. Embodiments may include retrieving historical health data for the user. A temporal factor for the historical health data can be derived. Estimated health data may be computed for a time duration corresponding to a data gap, based on the temporal factor. In the example, it is determined that, in general, about 1 hour (60 minutes) of activity is detected per day. This determination may be based on an average of historical data. On Thursday, though, it is detected that there is a data gap since the detected 11 minutes of activity is well below the typical duration of 1 hour. Accordingly, at 658, 49 minutes is added on Thursday to supplement the 11 minutes of the day, providing 60 minutes of combined actual and estimated exercise.

Figure 7:
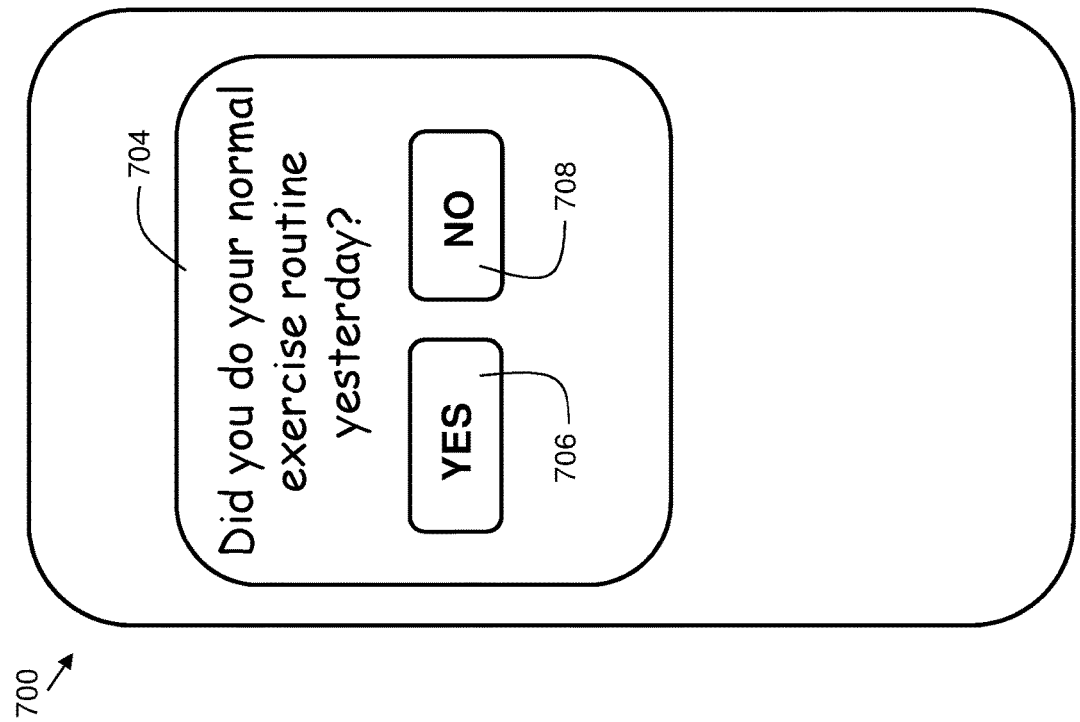
FIG. 7 shows an example of a confirmation user interface for a data gap in accordance with embodiments of the present invention.

FIG. 7 shows an example of a confirmation user interface 700 for a data gap in accordance with embodiments of the present invention. In embodiments, a user interface for a data gap is shown on mobile device 104 (FIG. 1). User interface 700 includes a query 704, which in the example, recites, Did you do your normal exercise routine yesterday?" Two buttons are shown, including 706 for a positive affirmation/response and 708 for a negative response. The screen of the mobile device may be touch sensitive, so that a user can select one of the buttons using his/her finger or a stylus. Although the options are shown as buttons, in implementations, any suitable user input may be substituted, such as a slider, wheel, or other mechanism. In some embodiments, selection may be made via a keyboard, mouse, or other hardware.

Figure 8:
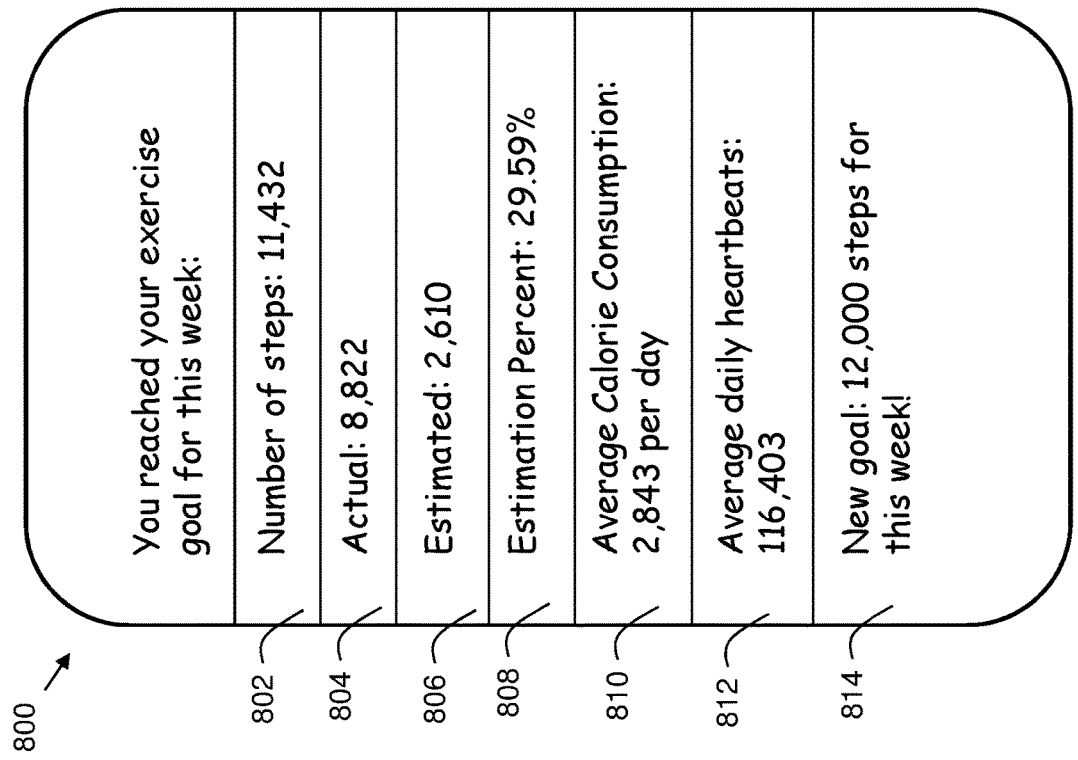
FIG. 8 shows an example of a fitness program adjustment based on a revised health parameter dataset, in accordance with embodiments of the present invention.

FIG. 8 shows an example of a fitness program adjustment based on a revised health parameter dataset, in accordance with embodiments of the present invention. Some embodiments include sending the revised health parameter dataset to a wearable electronic fitness tracking device, and initiating a fitness program adjustment based on the revised health parameter dataset. User interface 800 shows a summary of data used for an example fitness program adjustment. At 802, the number of steps detected is indicated as 11,432. At 804, the number of actual steps detected is indicated as 8,822. At 806, the estimated number of steps is indicated as 2,610. At 808, the estimation percent is indicated as 29.59%. At 810, the average calorie consumption per day is indicated as 2,843. At 812, the average daily heartbeats is indicated as 116,403. Based on the data, server 126 (FIG. 1), computes a new goal at 814. The new goal is 12,000 steps for the current week.

Figure 9:
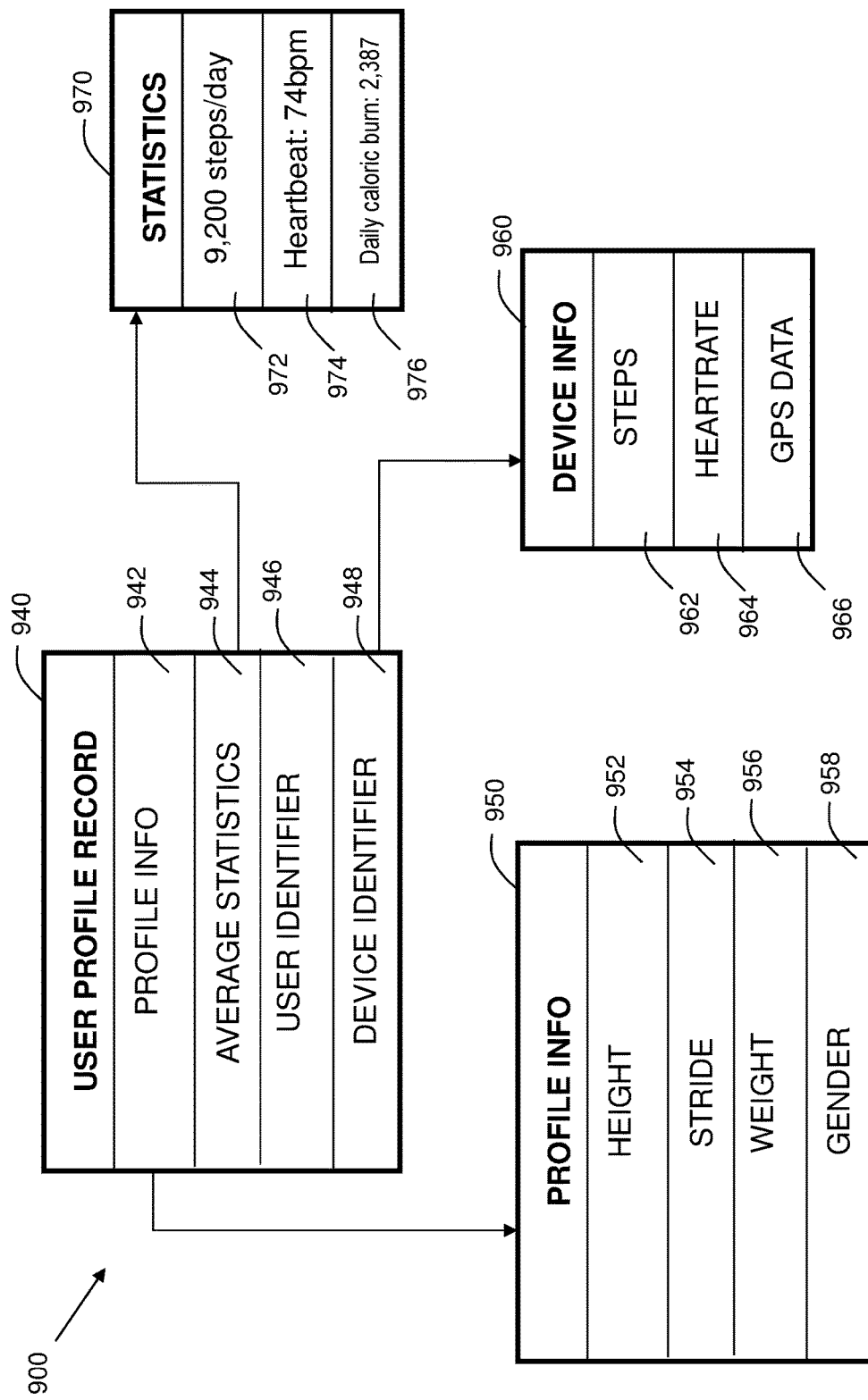
FIG. 9 shows examples of data structures used with embodiments for the present invention.

FIG. 9 shows examples of data structures used with embodiments for the present invention. Four data structures are shown: User profile record 940, profile info 950, device info 960 and statistics 970.

User profile record 940 includes profile information field 942, average statistics field 944, user identifier 946, and device identifier 948. The user identifier 946 may be an alphanumeric symbolic character set assigned to the user. In some embodiments, the profile data includes height data. In some embodiments, the profile data includes stride data. Profile info 950 includes height field 952 for the height data, stride field 954 for the stride data, weight field 956, and gender field 958. Height field 952 includes the user's height. Stride field 954 includes the length of a user's stride. Weight field 956 includes a user's weight. Gender field includes a user's gender. This information may be used by server 126 (FIG. 1) in calculating calorie consumption, distance traversed, and the like.

Statistics 970 includes data collected for the user. In the example, field 972 includes the user's steps per day of 9,200. Field 974 includes heartbeat data of 74 bpm. Field 976 includes daily calorie burn (consumption) of 2,387. These statistics may be measured by a wearable device, and may be used in providing estimated data during a data gap. As an example, if a user forgets to wear the device one day, heartbeat data, caloric burn data, and steps data measured on a previous day may be used for the estimated data.

The device identifier 948 may be an alphanumeric symbolic character set assigned to the wearable device associated with the user. Device info 960 may be used to store data retrieved from the wearable device. This data can include steps 962, heartrate 964, and GPS (distance, speed, and/or location) data 966.

Figure 10:
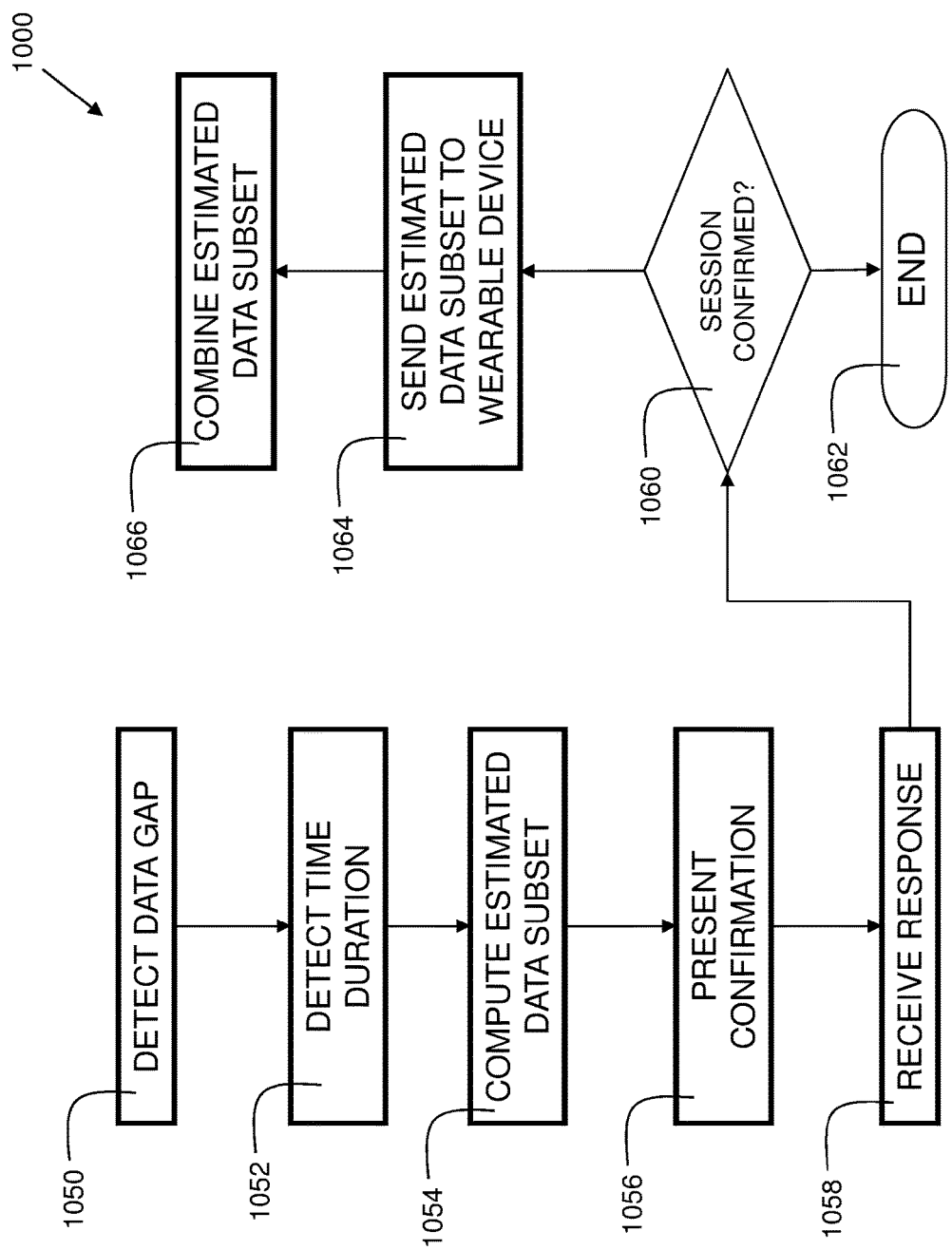
FIG. 10 is a flowchart indicating process steps for embodiments of the present invention.

FIG. 10 is a flowchart 1000 indicating process steps for embodiments of the present invention. At 1050, a data gap is detected from a health parameter dataset associated with a user. At 1052, a time duration corresponding to the data gap is detected. At 1054, an estimated data subset is computed for the missing data. At 1056, a confirmation user interface is presented for the data gap. At 1058, a response is received from the user. At 1060, it is determined, from the user interface, whether the session is confirmed. If the session is not confirmed, at 1062, the process ends. If at 1060, there is an affirmative confirmation, then at 1064, an estimated data subset is sent to the wearable device. At 1066, the estimated data subset is combined with (as a supplement to) the health parameter dataset to create a revised health parameter dataset.

As can now be appreciated, disclosed embodiments provide improvements to the technical field of health data management. Wearable electronic fitness tracking devices such as smart watches can collect vast amounts of data, including, but not limited to, steps taken, heartbeats, caloric expenditure, sleep patterns, heart rate, and/or other important biometric parameters. For various reasons, a user may not be wearing his/her wearable electronic fitness tracking device for a particular exercise session, or the device can stop working during an exercise session due to a low battery condition. These events can cause gaps in the health management dataset. Disclosed embodiments automatically detect and fill these gaps by using historical data, user profile parameters, crowdsourcing, and/or other techniques to derive an estimated data subset for the missing data, and combining the estimated data subset with the health parameter dataset to create a revised health parameter dataset. This allows a user to obtain a more accurate assessment of fitness activity, which can enable changes in fitness routines, thereby increasing the effectiveness of workouts, and improving overall health.

Some of the functional components described in this specification have been labeled as systems or units in order to more particularly emphasize their implementation independence. For example, a system or unit may be implemented as a hardware circuit comprising custom VLSI circuits or gate arrays, off-the-shelf semiconductors such as logic chips, transistors, or other discrete components. A system or unit may also be implemented in programmable hardware devices such as field programmable gate arrays, programmable array logic, programmable logic devices, or the like. A system or unit may also be implemented in software for execution by various types of processors. A system or unit or component of executable code may, for instance, comprise one or more physical or logical blocks of computer instructions, which may, for instance, be organized as an object, procedure, or function. Nevertheless, the executables of an identified system or unit need not be physically located together, but may comprise disparate instructions stored in different locations which, when joined logically together, comprise the system or unit and achieve the stated purpose for the system or unit.

Further, a system or unit of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices and disparate memory devices.

Furthermore, systems/units may also be implemented as a combination of software and one or more hardware devices. For instance, location determination and alert message and/or coupon rendering may be embodied in the combination of a software executable code stored on a memory medium (e.g., memory storage device). In a further example, a system or unit may be the combination of a processor that operates on a set of operational data.

As noted above, some of the embodiments may be embodied in hardware. The hardware may be referenced as a hardware element. In general, a hardware element may refer to any hardware structures arranged to perform certain operations. In one embodiment, for example, the hardware elements may include any analog or digital electrical or electronic elements fabricated on a substrate. The fabrication may be performed using silicon-based integrated circuit (IC) techniques, such as complementary metal oxide semiconductor (CMOS), bipolar, and bipolar CMOS (BiCMOS) techniques, for example. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor devices, chips, microchips, chip sets, and so forth. However, the embodiments are not limited in this context.

Also noted above, some embodiments may be embodied in software. The software may be referenced as a software element. In general, a software element may refer to any software structures arranged to perform certain operations. In one embodiment, for example, the software elements may include program instructions and/or data adapted for execution by a hardware element, such as a processor. Program instructions may include an organized list of commands comprising words, values, or symbols arranged in a predetermined syntax that, when executed, may cause a processor to perform a corresponding set of operations.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, may be non-transitory, and thus is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Program data may also be received via the network adapter or network interface.

Computer readable program instructions for carrying out operations of embodiments of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of embodiments of the present invention.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

While the disclosure outlines exemplary embodiments, it will be appreciated that variations and modifications will occur to those skilled in the art. For example, although the illustrative embodiments are described herein as a series of acts or events, it will be appreciated that the present invention is not limited by the illustrated ordering of such acts or events unless specifically stated. Some acts may occur in different orders and/or concurrently with other acts or events apart from those illustrated and/or described herein, in accordance with the invention. In addition, not all illustrated steps may be required to implement a methodology in accordance with embodiments of the present invention. Furthermore, the methods according to embodiments of the present invention may be implemented in association with the formation and/or processing of structures illustrated and described herein as well as in association with other structures not illustrated. Moreover, in particular regard to the various functions performed by the above described components (assemblies, devices, circuits, etc.), the terms used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of embodiments of the invention may have been disclosed with respect to only one of several embodiments, such feature may be combined with one or more features of the other embodiments as may be desired and advantageous for any given or particular application. Therefore, it is to be understood that the appended claims are intended to cover all such modifications and changes that fall within the true spirit of embodiments of the invention.

What is claimed is:

1. A wearable electronic fitness tracker device, in communication with a mobile device that is in communication with a social media system, the wearable electronic fitness tracker device comprising:
a processor;
a global positioning system (GPS) receiver;
a memory coupled to the processor, the memory containing instructions, that when executed by the processor, perform the steps of:
receiving a user height value and a user stride value into a user profile;
detecting a data gap from a health parameter dataset associated with a user, wherein the data gap is outside of a value predetermined as an amount of time a user sleeps each day;
determining a missing data time duration corresponding to the data gap;
detecting text from a post on a social media system of the user;
using natural language processing to analyze the text in the post;
determining keywords, based on the natural language processing;
detecting that the keywords are associated with an event indicating some activity associated with the missing data time duration that includes steps:
in response to the detecting, supplementing the data gap with an estimated data subset based in steps by:
computing an estimated data subset for the data gap, wherein the computing of the estimated data subset for the data gap is performed by:
determining, using the GPS receiver, a first location for the user, wherein the first location corresponds to a start of the data gap;
determining, using the GPS receiver, a second location for the user, wherein the second location corresponds to an end of the data gap;
determining a distance between the first location and second location; and
estimating a number of steps taken based on the distance, a user height value, and a user stride value;

presenting a confirmation user interface that includes a query to the user requesting confirmation relating to the estimated number of steps;

combining the estimated number of steps, as the data subset with the health parameter dataset to create a revised health parameter dataset in response to receiving affirmative confirmation, relating to the query, as user input; and initiating a fitness program adjustment based on the revised health parameter dataset;

wherein the electronic fitness tracker includes a tether, a wristband, or a ring.

2. The electronic computation device of claim 1, wherein the memory further comprises instructions, that when executed by the processor, perform the step of sending the revised health parameter dataset to a wearable electronic fitness tracking device.

3. The electronic computation device of claim 1, wherein the memory further comprises instructions, that when executed by the processor, perform the steps of:
identifying a periodic health parameter pattern; and
identifying an instance of a data gap that overlaps a period corresponding to the periodic health parameter pattern.

4. The electronic computation device of claim 1, wherein the memory further comprises instructions, that when executed by the processor, cause the electronic computation device to detect a data gap from a health parameter dataset by identifying an instance of a data gap time duration that exceeds a predetermined threshold.

5. The electronic computation device of claim 1, wherein the memory further comprises instructions, that when executed by the processor, cause the electronic computation device to:
identify a periodic health parameter pattern; and
identify an instance of a data gap that overlaps a period corresponding to the periodic health parameter pattern.

6. The electronic computation device of claim 1, wherein the memory further comprises instructions, that when executed by the processor, cause the electronic computation device to detect missing data from a health parameter dataset by:
retrieving historical health data for the user; and
using the historical health data as the estimated data subset.

7. The electronic computation device of claim 1, wherein the memory further comprises instructions, that when executed by the processor, cause the electronic computation device to compute an estimated data subset for the data gap by:
retrieving historical health data for the user;
deriving a temporal factor for the historical health data; and
computing estimated health data for the time duration corresponding to the data gap, based on the temporal factor.

8. The electronic computation device of claim 1, wherein the memory further comprises instructions, that when executed by the processor, cause the electronic computation device to:
present a confirmation user interface for the data gap; and
wherein combining the estimated data subset with the health parameter dataset to create a revised health parameter dataset is performed in response to receiving an affirmative confirmation from the confirmation user interface.

9. A computer program product for an electronic fitness tracker device, wherein the electronic fitness tracker device is in communication with a mobile device that is in communication with a social media system, the computer program product comprising a computer readable storage medium having program instructions embodied therewith, the program instructions executable by a processor to cause the electronic fitness tracking device to:
receive a user height value and a user stride value into a user profile;
detect a data gap from a health parameter dataset associated with a user, wherein the data gap is outside of a value predetermined as an amount of time a user sleeps each day;
determine a missing data time duration corresponding to the data gap;
detecting text from a post on a social media system of the user;
using natural language processing to analyze the text in the post;
determining keywords, based on the natural language processing;
detecting that the keywords are associated with an event indicating some activity associated with the missing data time duration that includes steps:
in response to the detecting, supplementing the data gap with an estimated data subset based in steps by:
compute an estimated data subset for the data gap, wherein the computing of the estimated data subset for the data gap is performed by:
determine, using the GPS receiver, a first location for the user, wherein the first location corresponds to a start of the data gap;
determine, using the GPS receiver, a second location for the user, wherein the second location corresponds to an end of the data gap;
determine a distance between the first location and second location; and
estimate a number of steps taken based on the distance, a user height value, and a user stride value;
present a confirmation user interface that includes a query to the user requesting confirmation relating to the estimated number of steps;
combine the estimated number of steps, as the data subset with the health parameter dataset to create a revised health parameter dataset in response to receiving affirmative confirmation, relating to the query, as user input; and
initiate a fitness program adjustment based on the revised health parameter dataset;
wherein the electronic fitness tracker includes a tether, a wristband, or a ring.

10. The computer program product of claim 9, wherein the computer readable storage medium includes program instructions executable by the processor to cause the electronic computation device to send the revised health parameter dataset to a wearable electronic fitness tracking device.

11. The computer program product of claim 9, wherein the computer readable storage medium includes program instructions executable by the processor to cause the electronic computation device to:
identify a periodic health parameter pattern; and
identify a data gap that overlaps a period corresponding to the periodic health parameter pattern.

12. The computer program product of claim 9, wherein the computer readable storage medium includes program instructions executable by the processor to cause the electronic computation device to detect a data gap from a health parameter dataset by identifying an instance of a data gap time duration that exceeds a predetermined threshold.

13. The computer program product of claim 9, wherein the computer readable storage medium includes program instructions executable by the processor to cause the electronic computation device to detect missing data from a health parameter dataset by:
   retrieving historical health data for the user; and
   using the historical health data as the estimated data subset.

14. The computer program product of claim 9, wherein the computer readable storage medium includes program instructions executable by the processor to cause the electronic computation device to:
   present a confirmation user interface for the data gap; and
      wherein combining the estimated data subset with the health parameter dataset to create a revised health parameter dataset is performed in response to receiving an affirmative confirmation from the confirmation user interface.

* * * * *